(12) United States Patent
Zhong et al.

(10) Patent No.: US 10,981,882 B1
(45) Date of Patent: Apr. 20, 2021

(54) COMPOUND FOR INHIBITING IDO, A MANUFACTURING METHOD AND A USE THEREOF

(71) Applicant: Shanghai JOYU Pharmatech Ltd., Shanghai (CN)

(72) Inventors: Yan Zhong, Shanghai (CN); Xirong Cao, Shanghai (CN); Yonglin Wang, Shanghai (CN)

(73) Assignee: Shanghai JOYU Pharmatech Ltd., Shanghai (CN)

( * ) Notice: Subject to any disclaimer, the term of this patent is extended or adjusted under 35 U.S.C. 154(b) by 57 days.

(21) Appl. No.: 16/498,832

(22) PCT Filed: Apr. 5, 2018

(86) PCT No.: PCT/CN2018/082062
§ 371 (c)(1),
(2) Date: Sep. 27, 2019

(87) PCT Pub. No.: WO2018/184585
PCT Pub. Date: Oct. 11, 2018

(30) Foreign Application Priority Data

Apr. 7, 2017 (CN) .......................... 201710222609.7

(51) Int. Cl.
*C07D 271/04* (2006.01)
(52) U.S. Cl.
CPC ................. *C07D 271/04* (2013.01)
(58) Field of Classification Search
CPC .................................................. C07D 271/04
See application file for complete search history.

(56) References Cited

U.S. PATENT DOCUMENTS 9,789,094 B2 * 10/2017 Combs .................... A61P 17/02

FOREIGN PATENT DOCUMENTS

| CN | 106883194 A | 6/2017 |
|---|---|---|
| CN | 107304191 A | 10/2017 |
| CN | 106967005 B | 7/2019 |

OTHER PUBLICATIONS

International Search Report received for PCT Patent Application No. PCT/CN2018/082062, dated Jun. 29, 2018, 6 pages (3 pages of English translation of International Search Report and 3 pages of original International Search Report).

* cited by examiner

*Primary Examiner* — Kamal A Saeed
(74) *Attorney, Agent, or Firm* — Amster, Rothstein & Ebenstein LLP

(57) ABSTRACT

A compound for inhibiting IDO represented by the following general formula I,

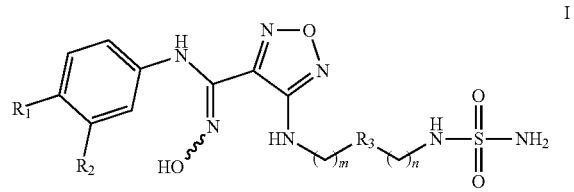

wherein a bond represented by a wavy line "〜〜〜" indicates the structure which represents independently a cis-isomer, a trans-isomer, or a mixture of cis- and trans-isomers; $R_1$ and $R_2$ are each independently selected from the group consisting of H, halogen, alkyl, alkoxyl, and haloalkyl; $R_3$ is selected from the group consisting of cyclopentyl, cyclohexyl, piperazinyl, and piperidyl; and the substitution positions of $R_3$ are optionally substituted at 1,2 position, 1,3 position or 1,4 position; m and n are an integer number independently selected from 0 to 5. The compound has a strong inhibiting effect on IDO and can be used to manufacture an IDO inhibitor for the prevention and/or treatment of an IDO-mediated disease with the pathologic features of the tryptophan metabolic pathway.

10 Claims, No Drawings

COMPOUND FOR INHIBITING IDO, A MANUFACTURING METHOD AND A USE THEREOF

This application is a National Stage entry under 35 U.S.C. 371 of International Patent Application No. PCT/CN2018/082062, filed on Apr. 5, 2018, which claims priority from Chinese Patent Application No. CN 201710222609.7, filed Apr. 7, 2017, the entire contents of each of which are incorporated by reference herein.

FIELD OF THE INVENTION

The invention belongs to the field of medicine and relates to a compound that can inhibit IDO, its preparation method as well as its application in the treatment of an IDO mediated disease with the pathologic features of the tryptophan metabolism pathway. The disease includes cancer, Alzheimer's disease, autoimmune disease, depression, anxiety disorder, cataract, psychological disorder, AIDS, etc.

BACKGROUND OF THE INVENTION

Cancer is one of the major diseases which seriously endangers human life, with more than half of which occurs in developing countries. The incidence rate of cancer in China is on the rise, increasing at an average annual growth rate of 3% to 5%. It is estimated that in China by 2020, there will have been 4 million people with cancer, with a mortality of 3 million thereof. The main reasons may be aging, urbanization, industrialization and lifestyle changes. In Chinese hospital drug market, the volume of cancer drugs has been growing steadily in recent years, reaching to 66.42 billion CNY in 2012, with a year-on-year growth of 13.07%. It was forecasted that by 2017, the market size of cancer drugs would have reached 105.57 billion CNY, with an annual growth rate of 7.57%.

Due to the unrestricted growth, invasion, and metastasis of malignant tumors, the three conventional clinical treatment methods (surgery, radiotherapy and chemotherapy) cannot completely remove or kill tumor cells, thus leading to frequent relapse. Tumor immunotherapy is the new application of modern biological technology and its related products. It has become the 4th approach for cancer prevention and treatment in light of its safety profile and efficacy. It can attain the anti-tumor effect by utilizing the host's natural defense mechanism (such as inhibition of tumor immune escape mechanism mediated by IDO) or providing highly targeted substance which is naturally produced.

Indoleamine 2,3-dioxygenase (IDO) is an intracellular monomer protein containing heme and is composed of 403 amino acid residues, including two folded α-helix domains. The domain contains catalytic pockets, where the substrate can be hydrophobic with IDO. IDO is a catalytic enzyme to make tryptophan into formylkynurenine, which is widely distributed in human and other mammals (rabbit and rat) tissues other than the liver tissue. IDO is the only rate-limiting enzyme outside of liver to catalyze the catabolism of tryptophan. The tryptophan is an essential amino acid to sustain the activation and proliferation of cells and also is an important and indispensable component to make up proteins. IDO is closely related to interferon (IFN), interleukin (IL), tumor necrosis factor and other cytokines, which can activate IDO under certain conditions. In a cell cycle of T-cells, there is a regulatory point that is very sensitive to the level of tryptophan. On the one hand, IDO depletes local tryptophan, resulting in the stagnation of T-cells in the middle of the GI phase, thereby inhibiting the proliferation of T-cells. On the other hand, kynurenine, the major product of tryptophan metabolism catalyzed by IDO, makes the changes of intracellular oxidants and antioxidants which are mediated by oxygen free radicals and induces the apoptosis of T-cells, which is an inherent immunosuppression mechanism in a body. A large number of studies have shown that IDO is highly expressed in leukemia cells, which inhibits local T-cell proliferation and T-cell-mediated immune response, and obstructs the transduction of T-cell activation signal, thus mediating tumor cells escape from immune system attack. IDO has been found to be constitutively expressed in most human tumors. Therefore, IDO is a potential target for cancer immunotherapy.

In addition, IDO is widely distributed in many human and animal tissues, catalyzing the catabolism of tryptophan along the kynurenine pathway (KP) to produce some metabolites including the neurotoxin quinolinic acid (QUIN). IDO and KP play a crucial role in the pathogenesis of Alzheimer's disease and depression. It also has the function of immune tolerance. IDO on tumor cells and antigen-presenting cells can induce the immune tolerance of T cells against tumor antigens. At present, IDO has been proved to be an important drug target. With the new drug target and the novel mechanism, IDO inhibitor can be applied to treat cancer, Alzheimer's disease, depression, cataract, and other major diseases, and has profound social and economic benefits. Currently, the research and development of IDO inhibitor drugs are just in full swing globally.

Published patent applications for selective inhibition of IDO include WO2004094409, WO2006122150, WO2007075598, WO20IDO05958 and WO2014066834, etc.

IDO inhibitors have a good application prospect in the pharmaceutical industry, but there is still no good candidate approved for the market. In order to achieve better cancer treatment effect and better meet the market demand, we hope to develop a new generation of selective IDO inhibitors with higher efficacy and low toxicity. The invention provides a novel selective IDO inhibitor with such structures which exhibits an excellent pharmaceutical profile.

SUMMARY OF THE INVENTION

The present invention aims to provide an efficient and low toxic compound which can selectively inhibit indoleamine 2,3-dioxygenase (IDO).

In order to do this, the present invention provides a compound for inhibiting IDO, wherein the compound is represented by the following general formula I.

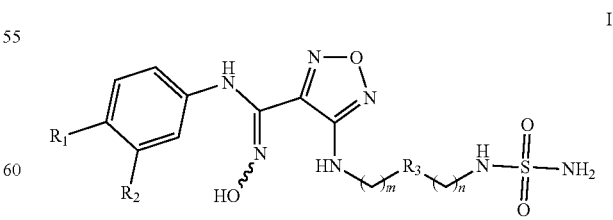

I wherein, a bond represented by a wavy line "〰〰" in formula I indicates the structure which represents a cis or a trans isomer, or a mixture of the cis and trans isomers; $R_1$ and $R_2$ are each independently selected from the group consisting of H, halogen, alkyl, alkoxy, and haloalkyl; $R_3$ is selected from the group consisting of cyclopentyl, cyclohexyl, piperazinyl, and piperidyl; and the substitution positions of $R_3$ are optionally substituted at 1, 2-positions, 1, 3-positions or 1, 4-positions; and m and n are an integer number independently selected from 0 to 5. The said substitution position refers to the site of $R_3$ (cyclopentyl, cyclohexyl, piperazinyl, piperidinyl) connecting to the other two groups (1,2,5-oxadiazole amino groups and amino sulfonamido groups, respectively).

Preferably, the halogen is F, Cl or Br, the alkyl is the alkyl of 1-5 carbons, the alkoxy is the alkoxyl of 1-5 carbons, the haloalkyl is the haloalkyl of 1-5 carbons.

Preferably, the alkyl is methyl, the alkoxy is methoxy, the haloalkyl is trifluoromethyl; $R_3$ is cyclohexyl, and the substitution position of $R_3$ is at 1,4-position; m is 0, 1 or 2; n is 0, 1 or 2.

Preferably, $R_1$ is F; $R_2$ is Br; $R_3$ is cyclohexyl, and the substitution position of $R_3$ is at 1,4-position; both m and n are 0.

Preferably, the compounds include the following compounds:

1

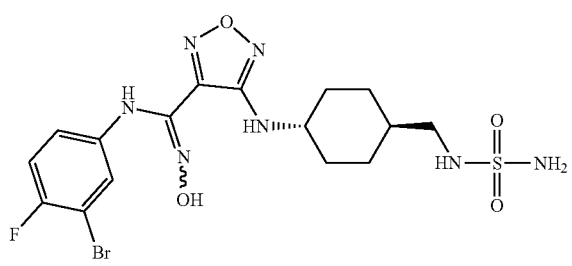

2

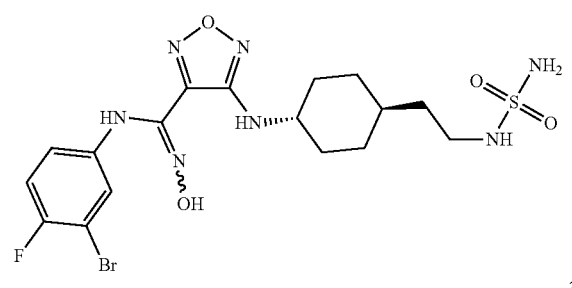

3

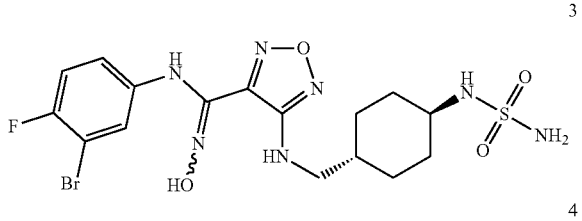

4

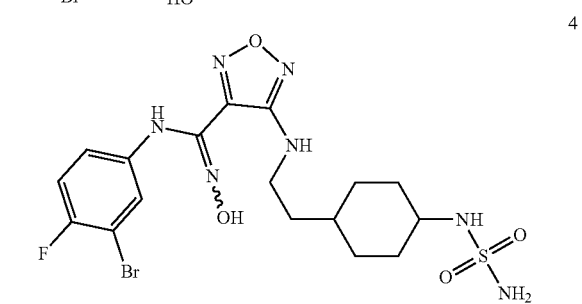

-continued

5

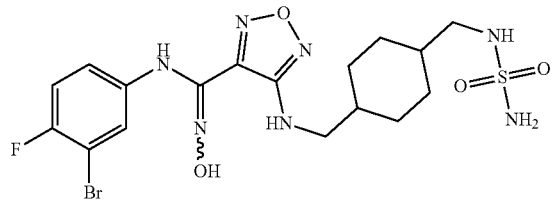

6

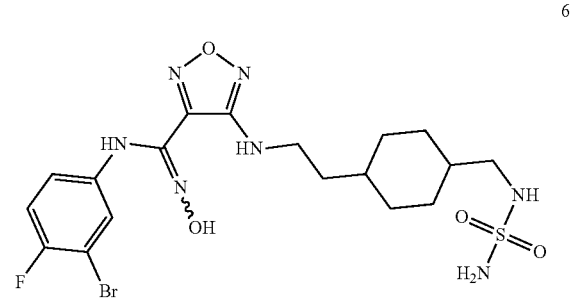

7

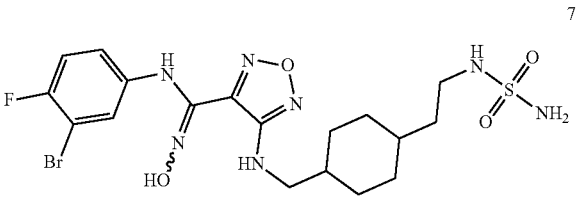

8

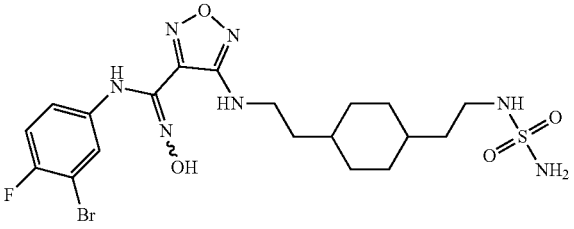

9

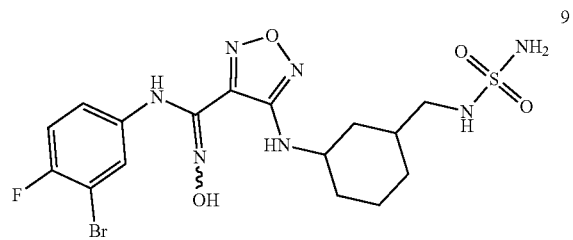

10

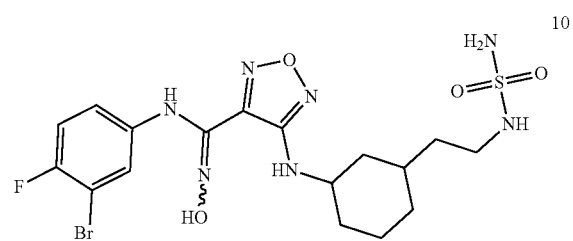

11
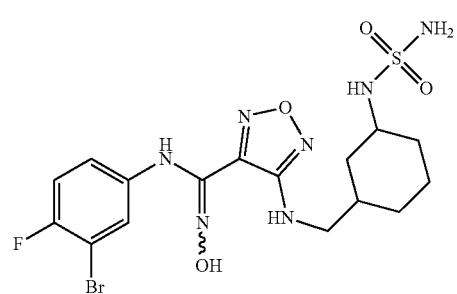
12
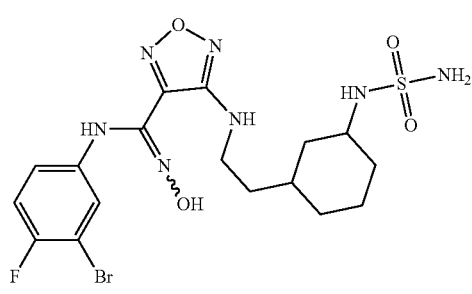
13
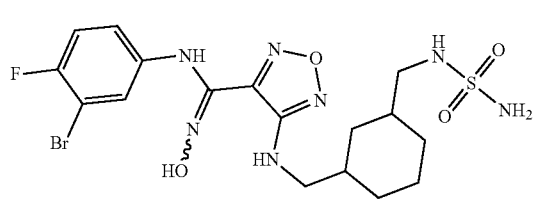
14
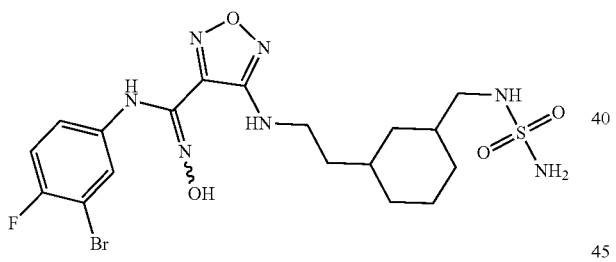
15
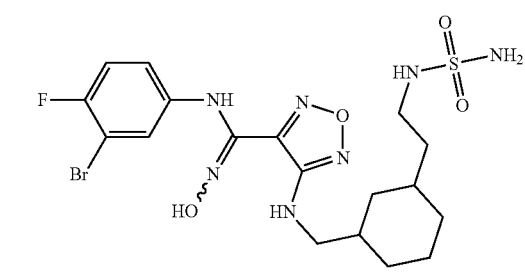
16
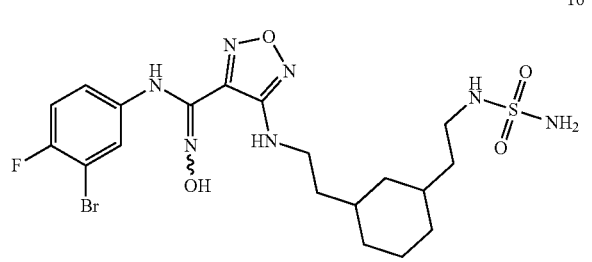
17
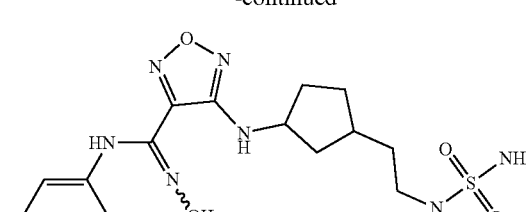
18
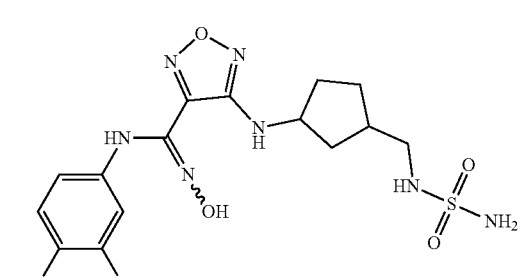
19
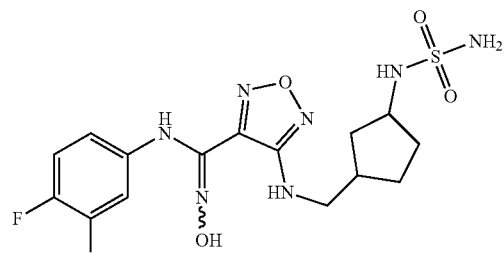
20
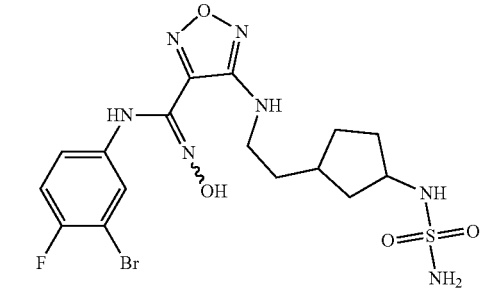
21
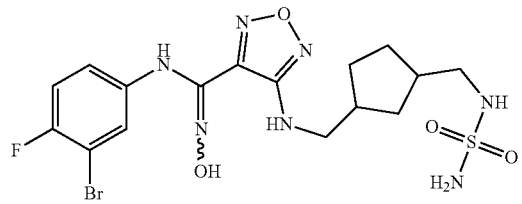
22
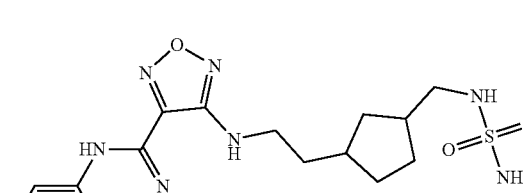

23
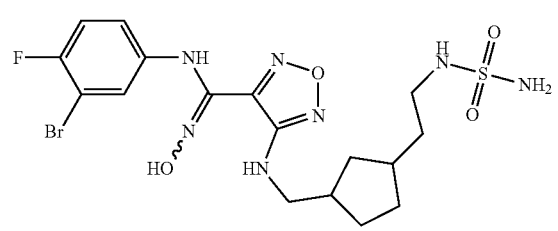
24
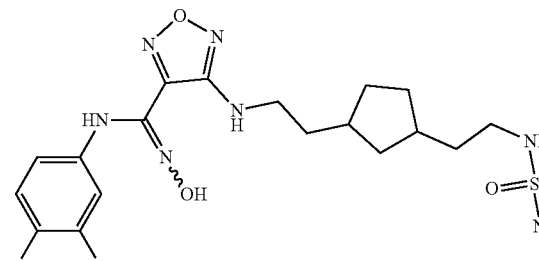
25
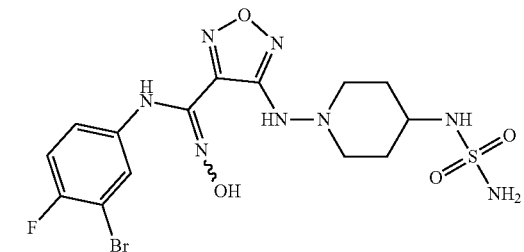
26
27
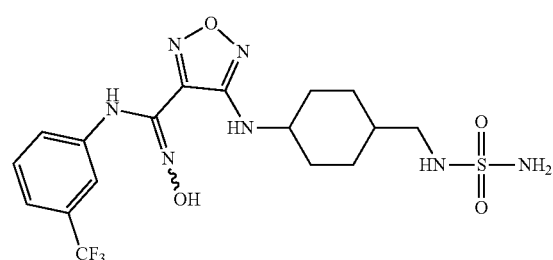
28
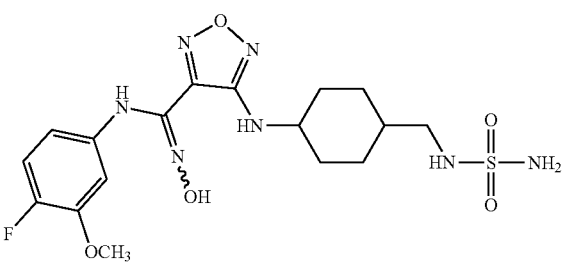
29
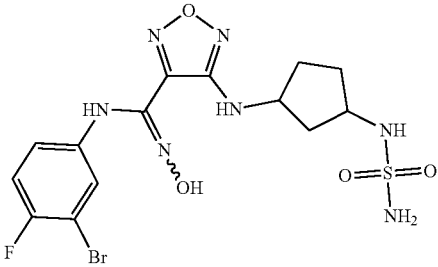
30
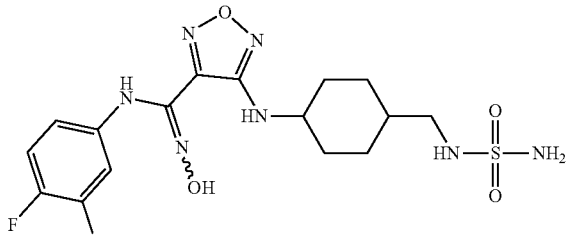
31
32
33
34
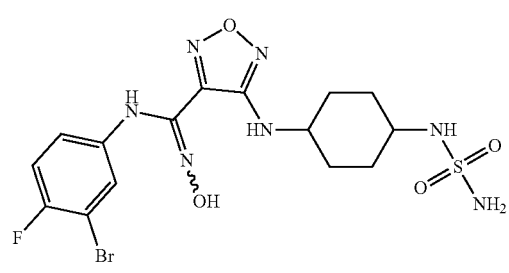

-continued

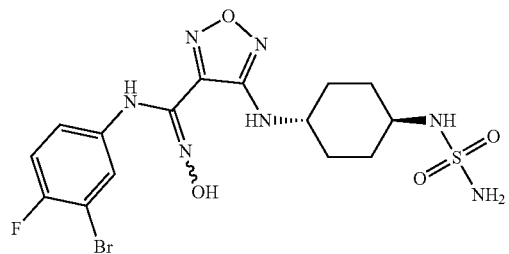
35

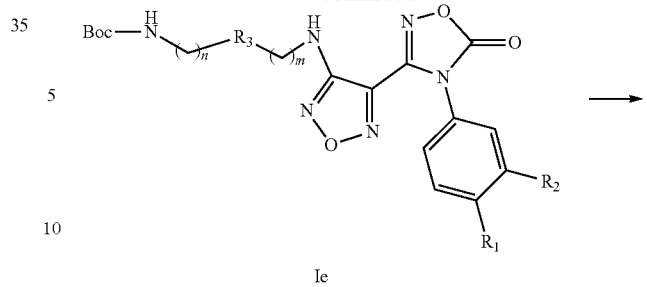
Ie

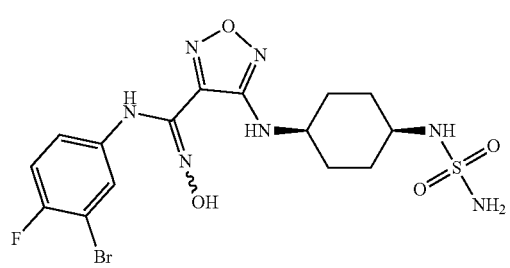
36

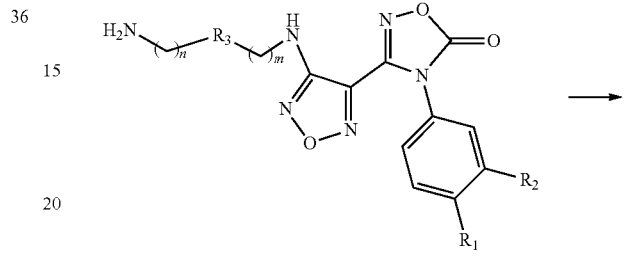
If

The present invention also provides a method of producing the compound for inhibiting IDO, which is prepared through the following route:

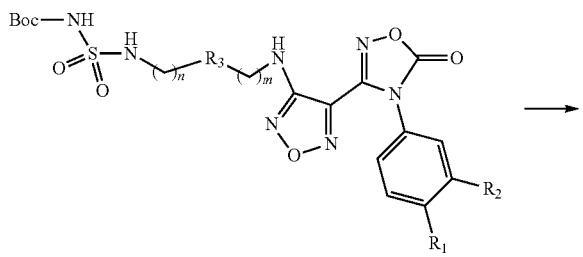
Ig

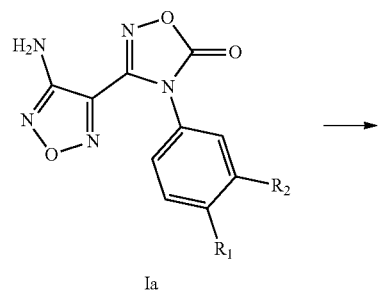
Ia

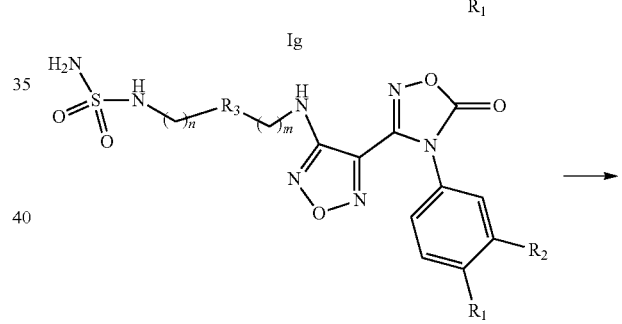
Ih

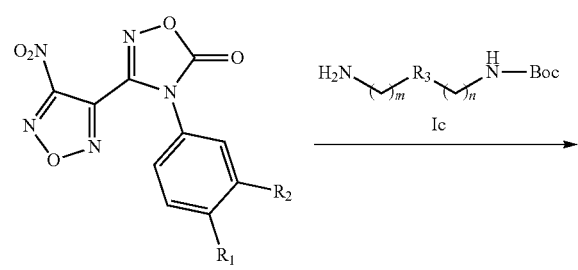
Ib

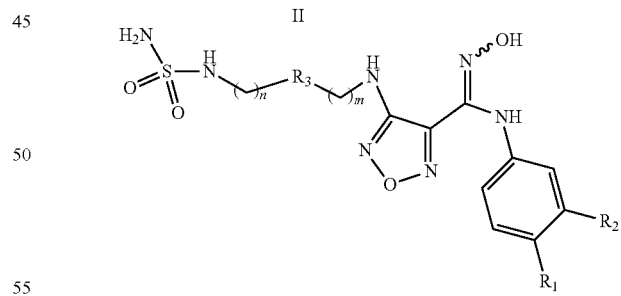
I

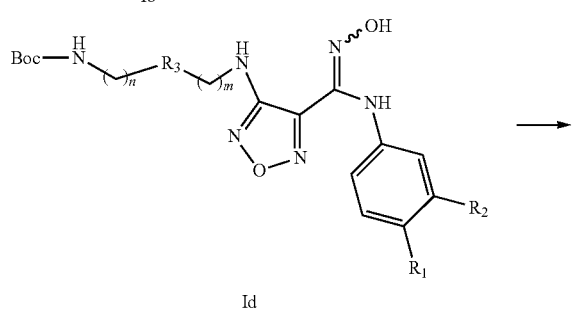
Id

The present invention also provides a use of a compound for inhibiting IDO, wherein, the compound can be used for the preparation of pharmaceutical composition which can prevent and/or treat an IDO-mediated disease with the pathologic features of the tryptophan metabolic pathway.

"Pharmaceutical composition" represents a composition comprising one or more of the above-mentioned compounds or a physiologically/pharmaceutically acceptable salt or prodrug thereof and other chemical mixtures of components, and other components such as a physiological/pharmaceutically acceptable carriers and excipients. The object of the pharmaceutical composition is to promote the administration, facilitate the absorption of the active ingredient and consequently to exert biological activity.

Preferably, the pharmaceutical composition consists of an amount of the compound with therapeutic potency according to claims 1-5, wherein the compound is selected from the group consisting of the tautomer, raceme, enantiomer, diastereomer, or a mixture thereof, or pharmaceutically acceptable salts thereof, or one or more pharmaceutically-acceptable carrier, diluent or excipient.

Preferably, the IDO-mediated disease is cancer, myelodysplastic syndrome, Alzheimer's disease, autoimmune disease, depression, anxiety disorders, cataracts, psychological disorder, and AIDS.

Preferably, the cancer includes but not limited to hepatocellular carcinoma, bile duct carcinoma, nasopharyngeal carcinoma, breast cancer, cervical cancer, non-small cell lung cancer, small cell lung cancer, gastric cancer, esophageal cancer, colorectal cancer, pancreatic cancer, melanoma, oral cancer, renal cancer, bladder cancer, prostate cancer, osteosarcoma, ovarian, fallopian tube cancer, gastrointestinal stromal tumor, glioma, head and neck cancer, leukemia, lymphoma, multiple myeloma and myelodysplastic syndrome.

The present invention provides a compound for strongly inhibiting IDO. The compound can be used for preparing an inhibitor of IDO which can prevent and/or treat an IDO-mediated disease with the pathologic features of the tryptophan metabolic pathway. The compound has a very good application prospect.

DETAILED DESCRIPTION OF A PREFERRED EMBODIMENT OF THE INVENTION

The present invention provides a compound for inhibiting IDO, wherein the compound is represented by the following general formula I:

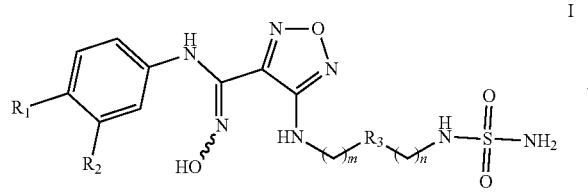

I wherein, a bond represented by a wavy line "〜〜〜" indicates the structure which represents independently a cis-isomer or a trans-isomer or a mixture of the cis and trans isomers; $R_1$ and $R_2$ are each independently selected from the group consisting of H, halogen, alkyl, alkoxyl, and haloalkyl; $R_3$ is selected from the group consisting of cyclopentyl, cyclohexyl, piperazinyl, and piperidyl; and the substitution positions of $R_3$ are optionally substituted at 1,2 positions, 1,3 positions or 1,4 positions; preferably, the substitution position of $R_3$ is substituted at 1,4 positions; m and n are an integer number independently selected from 0 to 5; preferably, m and n are independently selected from 0, 1 or 2.

The present invention provides a compound for inhibiting IDO, wherein the compound is represented by formula I, further including its tautomer, raceme, enantiomers, diastereomers, or a mixture thereof, or a pharmaceutically acceptable salt thereof.

As used herein, the term "pharmaceutically acceptable salt" refers to salts of the compound of the present invention, which has biological effectiveness and safety to a mamma.

Synthesis Method for the Compounds

The invention provides a process for preparing a compound of formula I, or a salt thereof as follow:

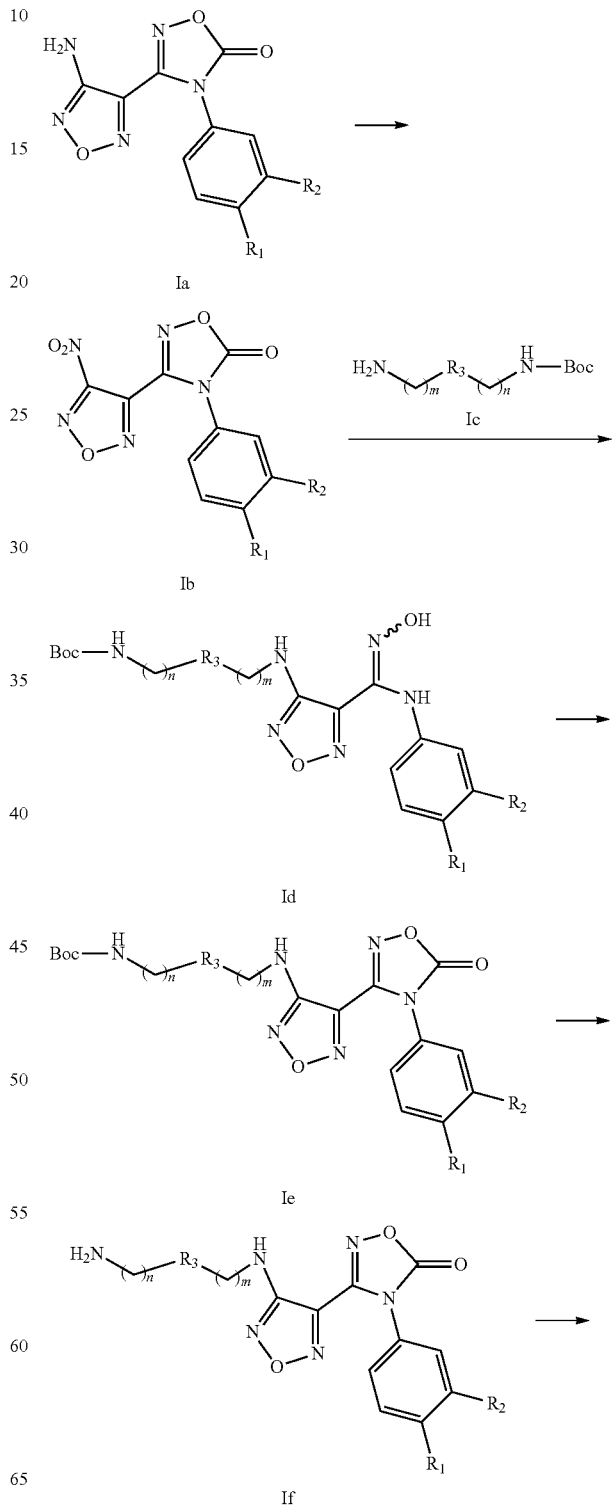

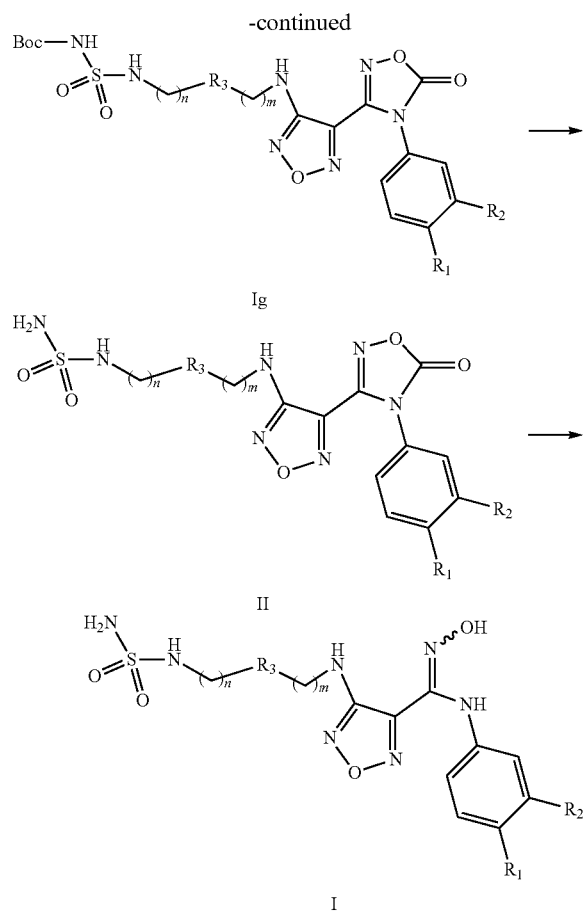

Under an acidic condition, the compound of formula (Ia) is oxidized to the compound of formula (Ib); then the compound of formula (Ib) is reacted with the compound of formula (Ic) under an alkaline condition to afford the compound of formula (Id). And then under an alkaline condition, cyclization of the compound of formula (Id) by heating forms the compound of formula (Ie), in which the base used is preferably N, N-carbonyl diimidazole. By remove of the amino protecting group under acidic conditions, the compound of formula (Ie) is transformed to the compound of formula (If), or a salt thereof, then the compound of formula (If) or its salt is reacted with an alcohol solution of chlorosulfonyl isocyanate in an alkaline solution at a low temperature to give the compound of formula (Ig). Preferably, the alcohol solution is a tert-butanol solution. The protective amino group in the compound of formula (Ig) is removed under an acidic condition to afford the compound of formula (Ih); finally opening the cycle of the compound of formula (Ih) in an alkaline condition to afford the desired compound of formula (I).

The base can be either an organic base or an inorganic base. The organic base includes but not limited to sodium bis(trimethylsilyl)amide, triethylamine, N, N-diisopropyl ethyl amine, n-butyl lithium, potassium t-butoxide, tetrabutylammonium bromide. The inorganic base includes but not limited to sodium hydride, sodium carbonate, sodium bicarbonate, potassium carbonate, potassium hydrogen carbonate or cesium carbonate.

The oxidizing agents include but not limited to hydrogen peroxide, potassium permanganate, and manganese dioxide.

The solvents used include but not limited to N, N-dimethylformamide, toluene, acetic acid, methanol, ethanol, tetrahydrofuran, methylene chloride, dimethyl sulfoxide, 1,4-dioxane or water.

The present invention is further described below with examples, but the examples are not limited to the scope of the present invention.

The structure of the compounds was identified through nuclear magnetic resonance (NMR) and/or the mass spectrometry.

The starting materials were either synthesized according to a method known in the art or purchased commercially.

As for the Example, the reactions were carried out under argon or nitrogen atmosphere unless otherwise stated.

As for the Example, the reaction solution refers to a solution of water unless otherwise stated.

As for the Example, the reaction temperature is room temperature in the range of 20° C. to 30° C. unless otherwise stated.

The reaction was monitored by thin-layer chromatography (TLC), and the developing solvents system used in the reaction comprise system A of methylene chloride and methanol system, system B of N-hexane and ethyl acetate system, system C of petroleum ether and ethyl acetate system, and system D of acetone. The volume ratio of the solvent is adjusted depending on the different polarity of the compounds.

For compounds purification, the eluent system through column chromatography or the developing solvents system through thin layer chromatography includes: system A of methylene chloride and methanol system, system B of N-hexane and ethyl acetate system, system C of N-hexane, ethyl acetate and methylene chloride system, system D of petroleum ether and ethyl acetate system, and system E of ethyl acetate. The volume ratio of the solvent is adjusted depending on the different polarity of the compounds. For some compounds, it is possible to add a small amount of triethylamine and acidic agents or alkaline agents and the like to adjust.

Example 1

The synthesis of the compound (1), trans-N-(3-bromo-4-fluorophenyl)-N'-hydroxy-4-((4-((sulfamoylamino) methyl) cyclohexyl)amino)-1,2,5-oxadiazole-3-carboximidamide (1), as follows:

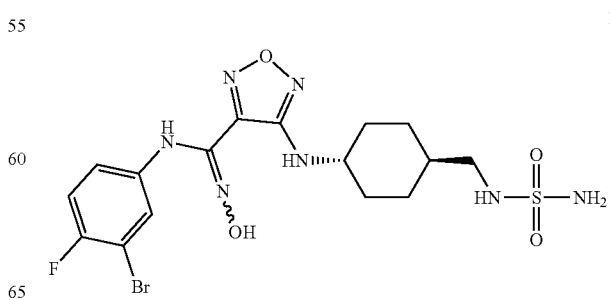

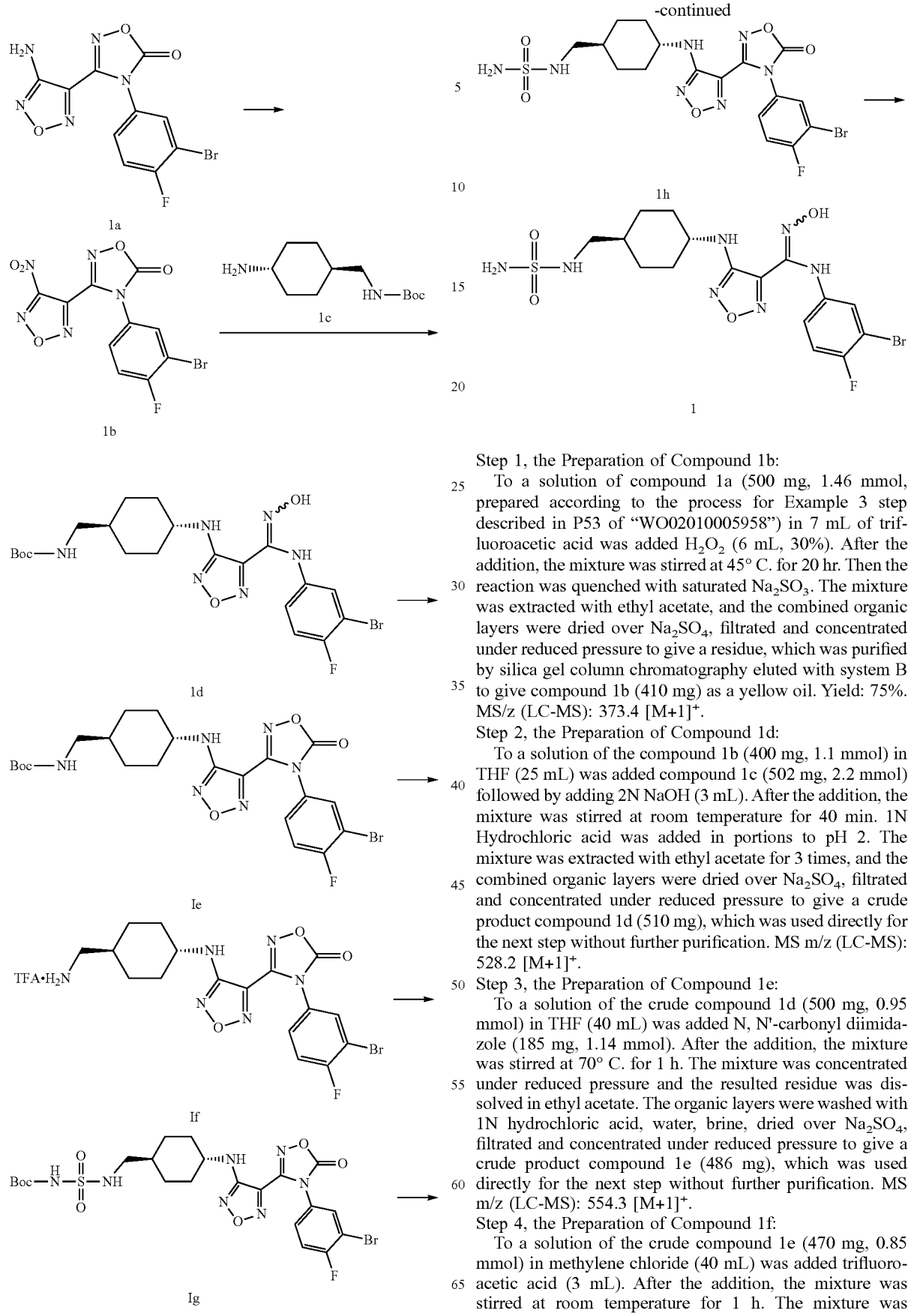

Step 1, the Preparation of Compound 1b:

To a solution of compound 1a (500 mg, 1.46 mmol, prepared according to the process for Example 3 step described in P53 of "WO02010005958") in 7 mL of trifluoroacetic acid was added $H_2O_2$ (6 mL, 30%). After the addition, the mixture was stirred at 45° C. for 20 hr. Then the reaction was quenched with saturated $Na_2SO_3$. The mixture was extracted with ethyl acetate, and the combined organic layers were dried over $Na_2SO_4$, filtrated and concentrated under reduced pressure to give a residue, which was purified by silica gel column chromatography eluted with system B to give compound 1b (410 mg) as a yellow oil. Yield: 75%. MS/z (LC-MS): 373.4 [M+1]$^+$.

Step 2, the Preparation of Compound 1d:

To a solution of the compound 1b (400 mg, 1.1 mmol) in THF (25 mL) was added compound 1c (502 mg, 2.2 mmol) followed by adding 2N NaOH (3 mL). After the addition, the mixture was stirred at room temperature for 40 min. 1N Hydrochloric acid was added in portions to pH 2. The mixture was extracted with ethyl acetate for 3 times, and the combined organic layers were dried over $Na_2SO_4$, filtrated and concentrated under reduced pressure to give a crude product compound 1d (510 mg), which was used directly for the next step without further purification. MS m/z (LC-MS): 528.2 [M+1]$^+$.

Step 3, the Preparation of Compound 1e:

To a solution of the crude compound 1d (500 mg, 0.95 mmol) in THF (40 mL) was added N, N'-carbonyl diimidazole (185 mg, 1.14 mmol). After the addition, the mixture was stirred at 70° C. for 1 h. The mixture was concentrated under reduced pressure and the resulted residue was dissolved in ethyl acetate. The organic layers were washed with 1N hydrochloric acid, water, brine, dried over $Na_2SO_4$, filtrated and concentrated under reduced pressure to give a crude product compound 1e (486 mg), which was used directly for the next step without further purification. MS m/z (LC-MS): 554.3 [M+1]$^+$.

Step 4, the Preparation of Compound 1f:

To a solution of the crude compound 1e (470 mg, 0.85 mmol) in methylene chloride (40 mL) was added trifluoroacetic acid (3 mL). After the addition, the mixture was stirred at room temperature for 1 h. The mixture was concentrated under reduced pressure to give a crude compound 1f (586 mg), which was used directly for the next step without further purification. MS m/z (LC-MS): 552.4 [M+1]+.

Step 5, the Preparation of Compound 1g:

To a solution of chlorosulfonyl isocyanate (0.793 g, 5.6 mmol) in methylene chloride (10 mL) was added t-BuOH (0.43 g, 5.8 mmol) at 0° C. After the addition, the mixture was stirred at 0° C. for 1 h to give mixture A. To a solution of the crude compound 1f (550 mg, 1.0 mmol) in methylene chloride (20 mL) was added triethylamine (0.75 mL) at 0° C. under $N_2$ to give mixture B. To the mixture B was added the mixture A at 0° C. After the addition, the mixture was stirred at 0° C. for 1 h. Then the reaction was quenched with saturated $NaHCO_3$ and was separated. The combined organic layers were orderly washed with water, brine, and then dried over $Na_2SO_4$, filtrated and concentrated under reduced pressure to give a residue, which was purified by thin-layer chromatography with the developing solvents system A to give compound 1g (217 mg, white solid), yield 34%. MS m/z (LC-MS): 633.5 [M+1]+.

Step 6, the Preparation of Compound 1h:

To a solution of the compound 1g (200 mg, 0.3 mmol) in methylene chloride (25 mL) was added trifluoroacetic acid (4 mL). After the addition, the mixture was stirred at room temperature for 1 h. After the reaction finished, the mixture was concentrated under reduced pressure to give crude compound 1h (210 mg), which was used directly for the next reaction without further purification. MS m/z (LC-MS): 533.4 [M+1]+.

Step 7, the Preparation of Compound 1:

To a solution of the crude compound 1h (200 mg, 0.38 mmol) in MeOH (20 mL) was added $K_2CO_3$ (230 mg, 1.67 mmol). After the addition, the mixture was stirred at 50° C. for 1 h. After the reaction finished, the reaction mixture was neutralized with brine and then separated. The water solution was extracted with ethyl acetate for 3 times. The combined organic layers were dried over $Na_2SO_4$, filtrated and concentrated under reduced pressure to give a residue, which was purified by thin-layer chromatography with the developing solvents system A to give the desired product 1 (45 mg, white solid), yield 24%.

MS m/z (ESI): 507.2 [M+1]+, $^1$HNMR (400 MHz, DMSO-d6) δ 11.54 (s, 1H), 8.89 (s, 1H), 7.11-7.25 (m, 3H), 6.78-6.79 (m, 1H), 6.68 (s, 2H), 6.23 (t, 1H), 2.43 (m, H), 1.21-1.82 (m, 9H), 3.24 (d, 2H).

Example 2

The synthesis of the compound (2), trans-N-(3-bromo-4-fluorophenyl)-N'-hydroxy-4-((4-(2-(sulfamoylamino) ethyl) cyclohexyl)amino)-1,2,5-oxadiazole-3-carboximidamide (2), as follows:

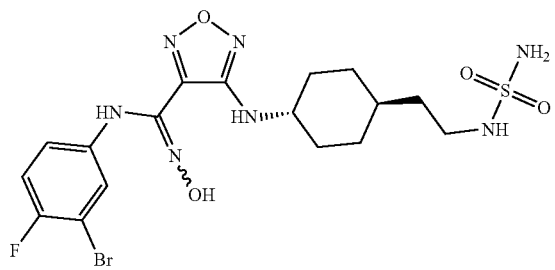

The title compound was prepared according to the procedure of Example 1, replacing the material compound 1c with

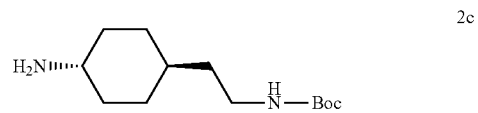 [SMILES: CC(C)(C)OC(=O)NCC[C@H]1CC[C@H](N)CC1]

(commercially available) in step 2, finally to obtain compound 2 (73 mg, white solid), yield 45%. MS m/z (ESI): 521.4 [M+1]+, $^1$HNMR (400 MHz, DMSO-d6) δ 11.52 (s, 1H), 8.87 (s, 1H), 7.09-7.27 (m, 3H), 6.76-6.79 (m, 1H), 6.67 (s, 2H), 6.21 (t, 1H), 2.41 (m, 1H), 1.20-1.83 (m, 11H), 3.55 (d, 2H).

Example 3

The synthesis of the compound (3), Trans-N-(3-bromo-4-fluorophenyl)-N'-hydroxy-4-(((4-(sulfamoylamino) cyclohexyl)methyl)amino)-1,2,5-oxadiazole-3-carboximidamide (3), as follows:

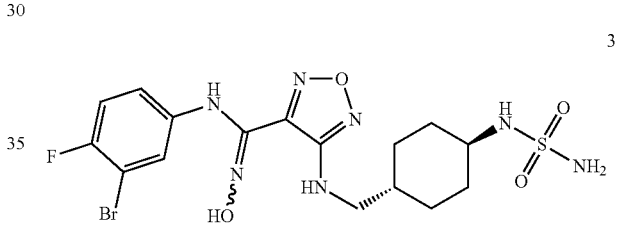

The title compound was prepared according to the procedure of Example 1, replacing the material compound 1c with

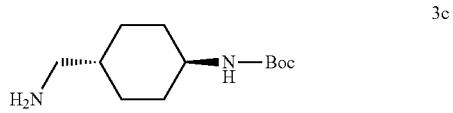

in step 2, finally to obtain compound 3 (47 mg, white solid), yield 38%. MS m/z (ESI): 507.2 [M+1]+, $^1$HNMR (400 MHz, DMSO-d6) δ 11.50 (s, 1H), 8.85 (s, 1H), 7.09-7.27 (m, 3H), 6.76-6.79 (m, 1H), 6.67 (s, 2H), 6.21 (t, 1H), 3.01 (m, 1H), 1.19-1.86 (m, 9H), 3.42 (d, 2H).

Example 4

The synthesis of the compound (4), N-(3-bromo-4-fluorophenyl)-N'-hydroxy-4-((2-(4-(sulfamoylamino) cyclohexyl)ethyl)amino)-1,2,5-oxadiazole-3-carboximidamide (4), as follows:

4

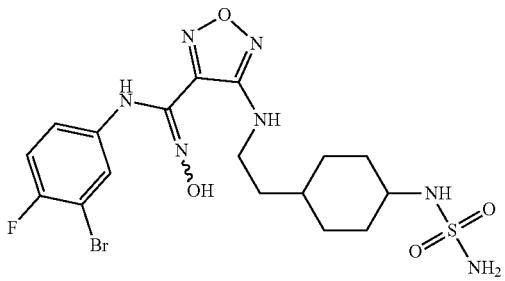

The title compound was prepared according to the procedure of Example 1, replacing the material compound 1c with

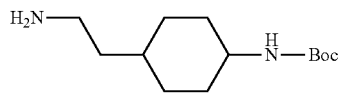

4c in step 2, finally to obtain compound 4 (36 mg, white solid), yield 34%. MS m/z (ESI): 521.4 [M+1]$^+$, $^1$HNMR (400 MHz, DMSO-d6) δ 11.49 (s, 1H), 8.87 (s, 1H), 7.11-7.29 (m, 3H), 6.75-6.80 (m, 1H), 6.68 (s, 2H), 6.23 (t, 1H), 3.05 (m, H), 1.20-1.91 (m, 11H), 3.81 (d, 2H).

Example 5

The synthesis of the compound (5), N-(3-bromo-4-fluorophenyl)-N'-hydroxy-4-(((4-((sulfamoylamino) methyl)cyclohexyl)methyl)amino)-1,2,5-oxadiazole-3-carboximidamide (5), as follows:

5

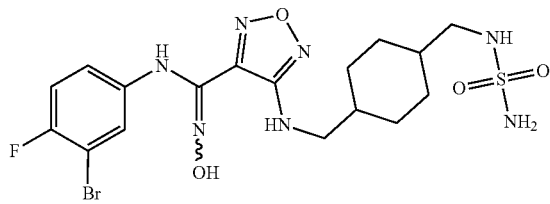

The title compound was prepared according to the procedure of Example 1, replacing the material compound 1c with

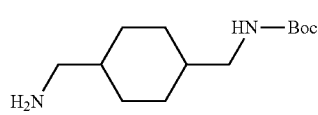

5c in step 2, finally to obtain compound 5 (47 mg, white solid), yield 39%. MS m/z (ESI): 521.4 [M+1]$^+$, $^1$HNMR (400 MHz, DMSO-d6) δ 11.52 (s, 1H), 8.88 (s, 1H), 7.11-7.30 (m, 3H), 6.77-6.81 (m, 1H), 6.69 (s, 2H), 6.22 (t, 1H), 1.21-2.05 (m, 10H), 3.51 (d, 2H), 3.23 (d, 2H).

Example 6

The synthesis of the compound (6), N-(3-bromo-4-fluorophenyl)-N'-hydroxy-4-((2-(4-((sulfamoylamino) methyl) cyclohexyl)ethyl)amino)-1,2,5-oxadiazole-3-carboximidamide (6), as follows:

6

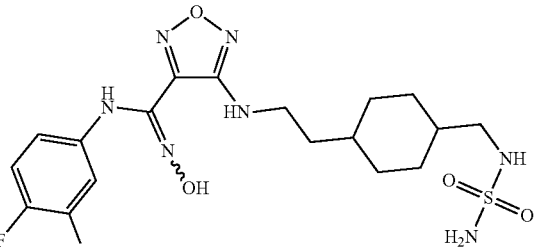

The title compound was prepared according to the procedure of Example 1, replacing the material compound 1c with

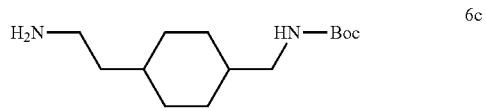 [SMILES: CC(C)(C)OC(=O)NCC1CCC(CCN)CC1]

6c in step 2, finally to obtain compound 6 (27 mg, white solid), yield 32%. MS m/z (ESI): 535.4 [M+1]$^+$, $^1$HNMR (400 MHz, DMSO-d6) δ 11.52 (s, 1H), 8.87 (s, 1H), 7.10-7.29 (m, 3H), 6.77-6.82 (m, 1H), 6.71 (s, 2H), 6.23 (t, 1H), 1.19-2.15 (m, 12H), 3.82 (d, 2H), 3.29 (d, 2H).

Example 7

The synthesis of the compound (7), N-(3-bromo-4-fluorophenyl)-N'-hydroxy-4-(((4-(2-(sulfamoylamino) ethyl) cyclohexyl)methyl)amino)-1,2,5-oxadiazole-3-carboximidamide (7), as follows:

7

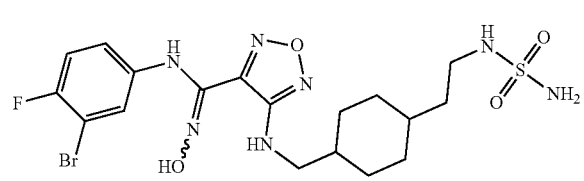

The title compound was prepared according to the procedure of Example 1, replacing the material compound 1c with

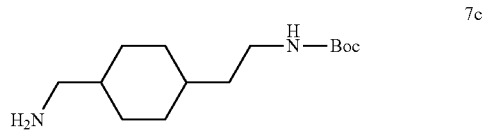

7c in step 2, finally to obtain compound 7 (38 mg, white solid), yield 32%. MS m/z (ESI): 535.4 [M+1]⁺, ¹HNMR (400 MHz, DMSO-d6) δ 11.50 (s, 1H), 8.86 (s, 1H), 7.11-7.28 (m, 3H), 6.79-6.84 (m, 1H), 6.70 (s, 2H), 6.25 (t, 1H), 1.24-2.11 (m, 12H), 3.84 (d, 2H), 3.54 (d, 2H).

Example 8

The synthesis of the compound (8), N-(3-bromo-4-fluorophenyl)-N'-hydroxy-4-((2-(4-(2-(sulfamoylamino) ethyl) cyclohexyl)ethyl)amino)-1,2,5-oxadiazole-3-carboximidamide (8), as follows:

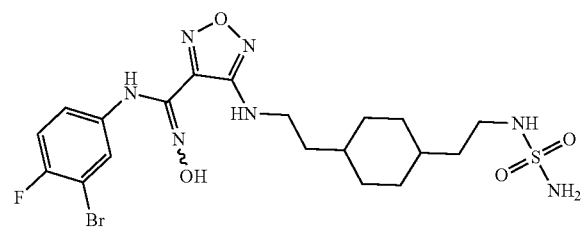

8

The title compound was prepared according to the procedure of Example 1, replacing the material compound 1c with

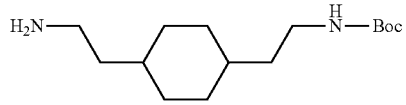

8c in step 2, finally to obtain compound 8 (42 mg, white solid), yield 39%. MS m/z (ESI): 549.3 [M+1]⁺, ¹HNMR (400 MHz, DMSO-d6) δ 11.53 (s, 1H), 8.88 (s, 1H), 7.10-7.26 (m, 3H), 6.80-6.86 (m, 1H), 6.71 (s, 2H), 6.26 (t, 1H), 1.24-2.11 (m, 14H), 4.04 (d, 2H), 3.52 (d, 2H).

Example 9

The synthesis of the compound (9), N-(3-bromo-4-fluorophenyl)-N'-hydroxy-4-((3-((sulfamoylamino)methyl) cyclohexyl)amino)-1, 2, 5-oxadiazole-3-carboximidamide (9), as follows:

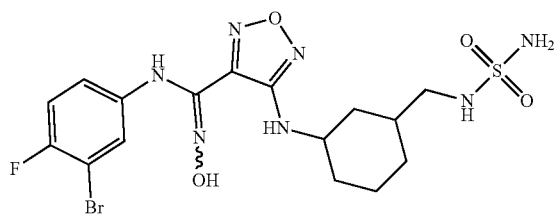

9

The title compound was prepared according to the procedure of Example 1, replacing the material compound 1c with

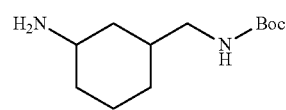

9c in step 2, finally to obtain compound 9 (52 mg, white solid), yield 47%. MS m/z (ESI): 507.2 [M+]⁺, ¹HNMR (400 MHz, DMSO-d6) δ 11.51 (s, 1H), 8.88 (s, 1H), 7.11-7.26 (m, 3H), 6.81-6.88 (m, 1H), 6.70 (s, 2H), 6.25 (t, 1H), 1.23-2.15 (m, 9H), 2.43 (d, 1H), 3.12 (d, 2H).

Example 10

The synthesis of the compound (10), N-(3-bromo-4-fluorophenyl)-N'-hydroxy-4-((3-(2-(sulfamoylamino)ethyl) cyclohexyl)amino)-1,2,5-oxadiazole-3-carboximidamide (10), as follows:

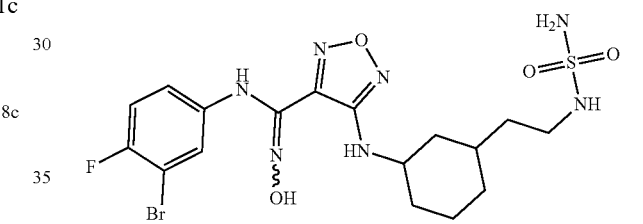

10

The title compound was prepared according to the procedure of Example 1, replacing the material compound 1c with

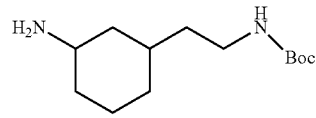

10c in step 2, finally to obtain compound 10 (39 mg, white solid), yield 31%. MS m/z (ESI): 521.4 [M+1]⁺, ¹HNMR (400 MHz, DMSO-d6) δ 11.52 (s, 1H), 8.86 (s, 1H), 7.10-7.27 (m, 3H), 6.80-6.89 (m, 1H), 6.71 (s, 2H), 6.23 (t, 1H), 1.23-2.21 (m, 11H), 2.41 (d, 1H), 3.42 (d, 2H).

Example 11

The synthesis of the compound (11), N-(3-bromo-4-fluorophenyl)-N'-hydroxy-4-(((3-(sulfamoylamino) cyclohexyl) methyl)amino)-1,2,5-oxadiazole-3-carboximidamide (11), as follows:

11

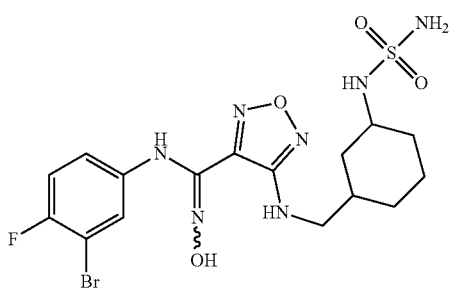

The title compound was prepared according to the procedure of Example 1, replacing the material compound 1c with 11c

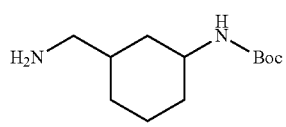

in step 2, finally to obtain compound 11 (27 mg, white solid, yield 15%. MS m/z (ESI): 507.2 [M+1]$^+$, $^1$HNMR (400 MHz, DMSO-d6) δ 11.50 (s, 1H), 8.86 (s, 1H), 7.11-7.28 (m, 3H), 6.81-6.91 (m, 1H), 6.73 (s, 2H), 6.25 (t, 1H), 1.21-2.23 (m, 9H), 3.76 (d, 2H), 3.82 (d, 2H).

Example 12

The synthesis of the compound (12), N-(3-bromo-4-fluorophenyl)-N'-hydroxy-4-((2-(3-(sulfamoylamino) cyclohexyl)ethyl)amino)-1,2,5-oxadiazole-3-carboximidamide (12), as follows:

12

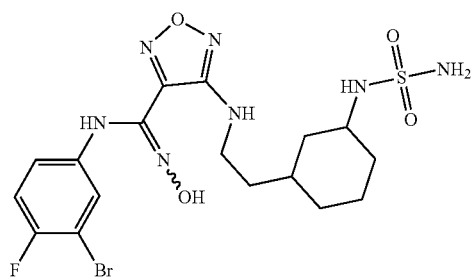

The title compound was prepared according to the procedure of Example 1, replacing the material compound 1c with 12c

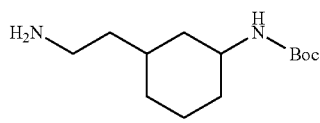

in step 2, finally to obtain compound 12 (44 mg, white solid), yield 35%. MS m/z (ESI): 521.4 [M+1]$^+$, $^1$HNMR (400 MHz, DMSO-d6) δ 11.48 (s, 1H), 8.84 (s, 1H), 7.09-7.29 (m, 3H), 6.80-6.92 (m, 1H), 6.72 (s, 2H), 6.23 (t, 1H), 1.21-2.23 (m, 9H), 3.76 (d, 2H), 3.82 (d, 2H).

Example 13

The synthesis of the compound (13), N-(3-bromo-4-fluorophenyl)-N'-hydroxy-4-(((4-((sulfamoylamino)methyl) cyclohexyl)methyl)amino)-1,2,5-oxadiazole-3-carboximidamide (13), as follows:

13

The title compound was prepared according to the procedure of Example 1, replacing the material compound 1c with 13c

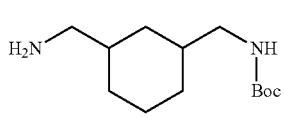

in step 2, finally to obtain compound 13 (27 mg, white solid), yield 18%. MS m/z (ESI): 521.4 [M+1]$^+$, $^1$HNMR (400 MHz, DMSO-d6) δ 11.50 (s, 1H), 8.83 (s, 1H), 7.10-7.31 (m, 3H), 6.81-6.95 (m, 1H), 6.71 (s, 2H), 6.22 (t, 1H), 1.20-2.21 (m, 10H), 3.51 (d, 2H), 3.26 (d, 2H).

Example 14

The synthesis of the compound (18), N-(3-bromo-4-fluorophenyl)-N'-hydroxy-4-((3-((sulfamoylamino)methyl) cyclopentyl)amino)-1,2,5-oxadiazole-3-carboximidamide (18), as follows:

18

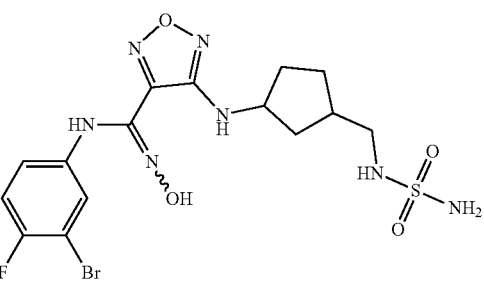

The title compound was prepared according to the procedure of Example 1, replacing the material compound 1c with

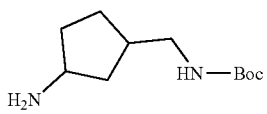

in step 2, finally to obtain compound 18 (42 mg, white solid), yield 34%. MS m/z (ESI): 507.7 [M+1]⁺, ¹HNMR (400 MHz, DMSO-d6) δ 11.49 (s, 1H), 8.82 (s, 1H), 7.11-7.29 (m, 3H), 6.81-6.97 (m, 1H), 6.71 (s, 2H), 6.25 (t, 1H), 2.53 (m, 1H), 1.17-2.21 (m, 7H), 3.33 (d, 2H).

Example 15

The synthesis of the compound (25), N-(3-bromo-4-fluorophenyl)-N'-hydroxy-4-((4-(sulfamoylamino)piperidin-1-yl)amino)-1,2,5-oxadiazole-3-carboximidamide (25), as follows:

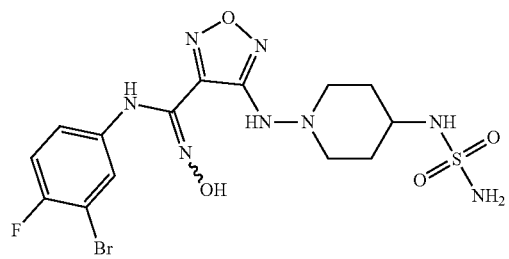

The title compound was prepared according to the procedure of Example 1, replacing the material compound 1c with

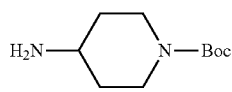

in step 2, finally to obtain compound 25 (36 mg, white solid), yield 29%. MS m/z (ESI): 494.6 [M+1]⁺, ¹HNMR (400 MHz, DMSO-d6) δ 11.50 (s, 1H), 9.01 (s, 1H), 7.12-7.31 (m, 3H), 6.80-6.94 (m, 1H), 6.72 (s, 2H), 6.26 (t, 1H), 2.56 (m, 1H), 1.70-2.23 (m, 4H), 2.62-2.83 (m, 4H).

Example 16

The synthesis of the compound (29), N-(3-bromo-4-fluorophenyl)-N'-hydroxy-4-((3-(2-(sulfamoylamino)ethyl) cyclopentyl)amino)-1,2,5-oxadiazole-3-carboximidamide (29), as follows:

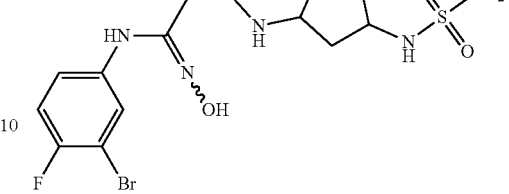

The title compound was prepared according to the procedure of Example 1, replacing the material compound 1c with

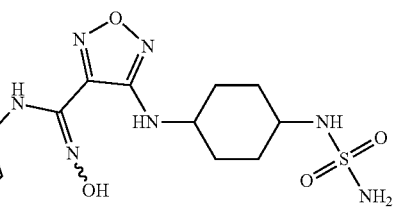

in step 2, finally to obtain compound 29 (26 mg, white solid), yield 19%. MS m/z (ESI): 479.3 [M+1]⁺, ¹HNMR (400 MHz, DMSO-d6) δ 11.48 (s, 1H), 8.81 (s, 1H), 7.09-7.30 (m, 3H), 6.80-6.95 (m, 1H), 6.72 (s, 2H), 6.24 (t, 1H), 2.41-2.43 (m, 2H), 1.68-2.19 (m, 6H).

Example 17

The synthesis of the compound (34), N-(3-bromo-4-fluorophenyl)-N'-hydroxy-4-((4-(sulfamoylamino) cyclohexyl)amino)-1,2,5-oxadiazole-3-carboximidamide (34), as follows:

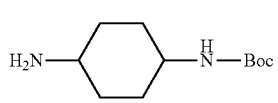

The title compound was prepared according to the procedure of Example 1, replacing the material compound 1c with (commercially available) in step 2, finally to obtain compound 34 (51 mg, white solid), yield 42%. MS m/z (ESI): 493.5 [M+1]⁺, ¹HNMR (400 MHz, DMSO-d6) δ 11.51 (s, 1H), 8.87 (s, 1H), 7.10-7.28 (m, 3H), 6.79-6.78 (m, 1H), 6.67 (s, 2H), 6.22 (t, 1H), 2.41 (m, 1H), 1.20-1.85 (m, 8H), 3.14 (m, 1H).

Example 18

The synthesis of the compound (35), trans-N-(3-bromo-4-fluorophenyl)-N'-hydroxy-4-(((1r,4r)-4-(sulfamoylamino)yclohexyl)amino)-1,2,5-oxadiazole-3-carboximidamide (35), as follows:

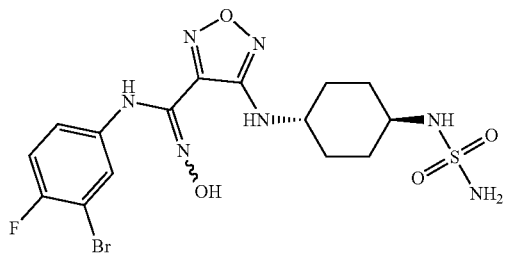

35

The title compound was prepared according to the procedure of Example 1, replacing the material compound 1c with

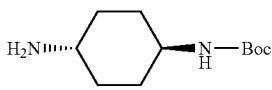

35c (commercially available) in step 2, finally to obtain compound 35 (43 mg, white solid), yield 37%. MS m/z (ESI): 493.5 [M+1]+, $^1$HNMR (400 MHz, DMSO-d6) δ 11.49 (s, 1H), 8.88 (s, 1H), 7.10-7.27 (m, 3H), 6.81-6.79 (m, 1H), 6.65 (s, 2H), 6.24 (t, 1H), 2.43 (m, 1H), 1.21-1.87 (m, 8H), 3.13 (m, 1H).

Example 19

The synthesis of the compound (36), cis-N-(3-bromo-4-fluorophenyl)-N'-hydroxy-4-(((1s,4s)-4-(sulfamoylamino)cyclohexyl)amino)-1,2,5-oxadiazole-3-carboximidamide (36), as follows:

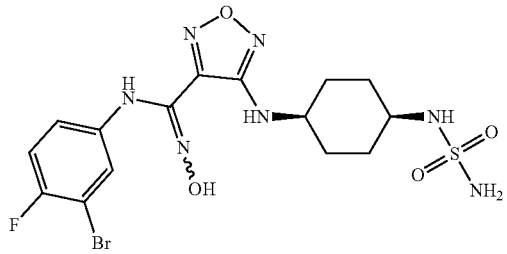

36

The title compound was prepared according to the procedure of Example 1, replacing the material compound 1c with

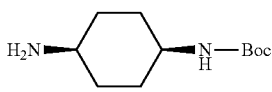

36c (commercially available) in step 2, finally to obtain compound 36 (38 mg, white solid), yield 30%. MS m/z (ESI): 493.5 [M+1]+, $^1$HNMR (400 MHz, DMSO-d6) δ 11.50 (s, 1H), 8.87 (s, 1H), 7.11-7.29 (m, 3H), 6.79-6.77 (m, 1H), 6.65 (s, 2H), 6.21 (t, 1H), 2.40 (m, 1H), 1.20-1.85 (m, 8H), 3.10 (m, 1H).

Biological Evaluation

1. Assay the Inhibitory Activity of the Compound Against Human IDO1 Protease

The inhibitory activity of extracorporal human IDO1 protease was tested through the following method. The inhibition effect of compounds of the present invention against the human IDO1 protease was determined through the method.

(1) Preparation of Human Recombinant IDO1 Protease

BL21 E. Coli were transformed with a correct sequences PET28a-hIDO1 vector. A single colony was inoculated in Luria-Bertani (LB) medium at 37° C. Bacterial cells were then collected through centrifugation. The cell pellets were sonicated, then centrifuged at 4° C. The supernatant was then collected and purified by Ni chromatography to give pure rhIDO1 protease.

(2) The Test of the Compounds

IDO1 enzymatic assay was carried out in a reaction mixture (500 μL/well) containing 50 mmol/L potassium phosphate buffer, 400 μg/mL catalase, 40 mmol/L ascorbic acid, 20 μmol/mL methylene blue, 300 mmol/L L-Tryptophan and the test compound. After the mixture was incubated for 3~5 min at 37° C., recombinant human IDO1 was added to. The mixture was incubated for another 30 min at 37° C. and the reaction was stopped by adding 200 μL of 30% (w/v) trichloroacetic acid. After heating in a water bath pot at 65° C. for 15 min and centrifugation at 13800×g for 10 min. 100 μL of supernatant was transferred into a well of a 96-well microplate and mixed with the same volume of 2% (w/v) p-(dimethylamino)benzaldehyde in acetic acid. Then kynurenine was added. When the color of the mixture became yellow, the mixture was measured for absorbance (D) value at 480 nm using microplate reader.

The inhibitory activity of compounds of the present invention against the human IDO1 protease was determined with the above test. The resulting $IC_{50}$ values are shown in Table 1.

TABLE 1

The inhibitory activity of the compounds in Example 1-19 against human IDO1 protease

| Example number | $IC_{50}$ (nM) |
| --- | --- |
| 1 | 16 |
| 2 | 46 |
| 3 | 38 |
| 4 | 22 |
| 5 | 45 |
| 6 | 48 |
| 7 | 74 |
| 8 | 51 |
| 9 | 64 |
| 10 | 59 |
| 11 | 43 |
| 12 | 60 |
| 13 | 72 |
| 14 | 108 |
| 15 | 83 |
| 16 | 63 |
| 17 | 15 |
| 18 | 6 |
| 19 | 12 |

It is obvious that the compounds in Example 1-19 have significant inhibitory activity against human IDO1 protease.

2. Determination of the Inhibitory Activity of IDO Protease in HEK293 Cell

HEK293 cells were seeded in a 96-well microplate at a density of 2.5×10⁴ cells/well and were maintained in DMEM (containing 10% fetal bovine serum, 50 U/mL penicillin and 50 mg/mL streptomycin) at 37° C. 24 hours later, HEK-293 cells were transfected with pcDNA3.1 (+)-hIDO vector carrying human IDO gene using Lipofectamine 2000. After 24 hr, the tested compounds were added to the cells and incubated for 5 hr. 140 µL of supernatant was transferred to a well in a new 96-well microplate. 10 µL of 30% (w/v) trichloroacetic acid was added to each sample-containing well and reaction was incubated at 65° C. for 15 min. The reaction mixture was centrifuged at 13000×g for 10 min. The supernatant was mixed with p-(dimethylamino) benzaldehydein acetic acid in the same volume. The yellow pigment derived from kynurenine was measured for absorbance (D) value at 480 nm using a microplate reader.

The inhibitory activity of compounds prepared in Example 1-19 against the IDO protease in HEK293 cell was determined with the above test. The resulting $IC_{50}$ values are shown in Table 2.

TABLE 2

The inhibitory activity of compounds in Example 1-19 against IDO protease in HEK293 cell

| Example number | $IC_{50}$ (nM) |
|---|---|
| 1 | 8 |
| 2 | 36 |
| 3 | 13 |
| 4 | 36 |
| 5 | 14 |
| 6 | 39 |
| 7 | 21 |
| 8 | 45 |
| 9 | 27 |
| 10 | 52 |
| 11 | 18 |
| 12 | 23 |
| 13 | 32 |
| 14 | 48 |
| 15 | 37 |
| 16 | 42 |
| 17 | 10 |
| 18 | 3 |
| 19 | 5 |

It is obvious that the compounds in Example 1-19 have significant inhibitory activity against IDO protease in HEK293 cell.

Other compounds of 14, 15, 16, 17, 19, 20, 21, 22, 23, 24, 26, 27, 28, 30, 31, 32 and 33, were prepared according to the method of Example 1-19 and also showed the inhibiting effect on IDO protease tested by the above assay.

In summary, the present invention provided some new compounds represented by formula (I). These compounds were determined to have an excellent inhibiting effect for IDO protease, therefore can be used in the preparation of pharmaceutical composition to prevent and/or treat an IDO-mediated disease with the pathologic features of the tryptophan metabolic pathway.

Although the present invention has been described in detail through preferred examples, it should be appreciated that the description should not be taken for a limitation of the present invention. Modifications and replacements of the invention will be obvious after those skilled in the art have read the content. Accordingly, the scope of protection for the present invention should be indicated by the appended claims set out below.

What is claimed herein is:

1. A compound for inhibiting IDO, wherein the compound is represented by the following general formula I:

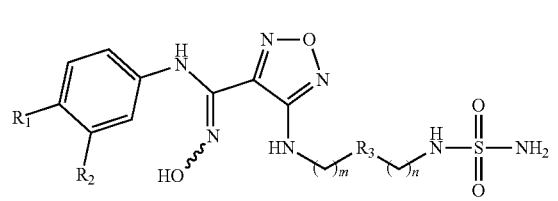

wherein, a bond represented by a wavy line "⁓" indicates a structure which represents independently a cis-isomer or a trans-isomer or a mixture of the cis and trans isomers; $R_1$ and $R_2$ are each independently selected from the group consisting of H, halogen, alkyl, alkoxyl, and haloalkyl; $R_3$ is selected from the group consisting of cyclopentyl, cyclohexyl, piperazinyl, and piperidyl, and the substitution positions of $R_3$ are optionally substituted at 1,2 position, 1,3 position or 1,4 position; m and n are each an integer number independently selected from 0 to 5.

2. The compound for inhibiting IDO according to claim 1, wherein the halogen is F, Cl, or Br; the alkyl is the alkyl of 1-5 carbons; the alkoxyl is the alkoxyl of 1-5 carbons; the haloalkyl is the haloalkyl of 1-5 carbons.

3. The compound for inhibiting IDO according to claim 2, wherein the alkyl is methyl; the alkoxyl is methoxyl; the haloalkyl is trifluoromethyl; $R_3$ is cyclohexyl, and the substitution position of $R_3$ is at 1,4 position; m is 0, 1 or 2; n is 0, 1 or 2.

4. The compound for inhibiting IDO according to claim 2, wherein $R_1$ and $R_2$ are each independently selected from the group consisting of F and Br; $R_3$ is cyclohexyl, and the substitution position of $R_3$ is at 1,4 position; Both m and n are 0.

5. The compound for inhibiting IDO according to claim 1, wherein the compound of formula I is selected from the following structures:

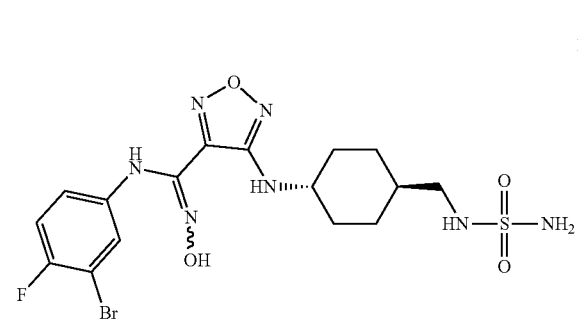

-continued
2
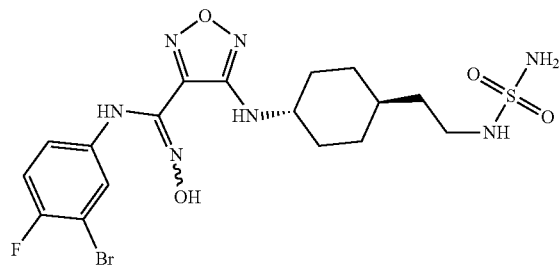
3
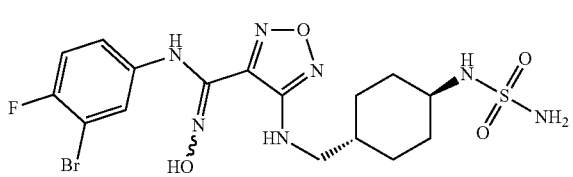
4
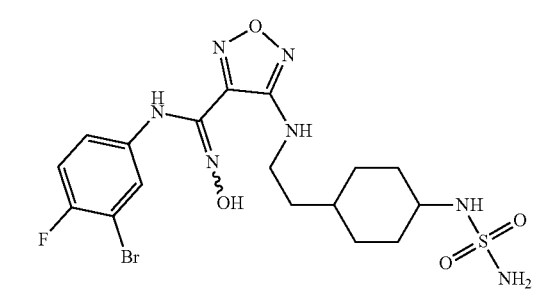
5
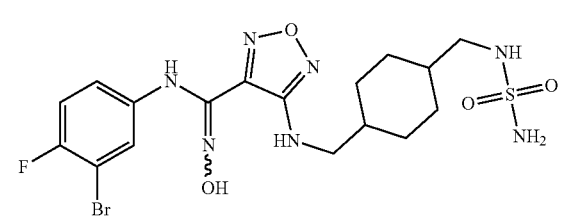
6
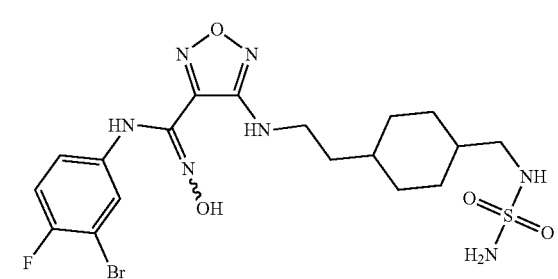
7
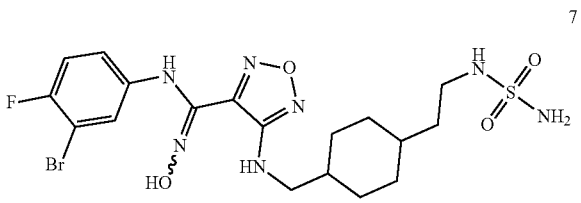
-continued
8
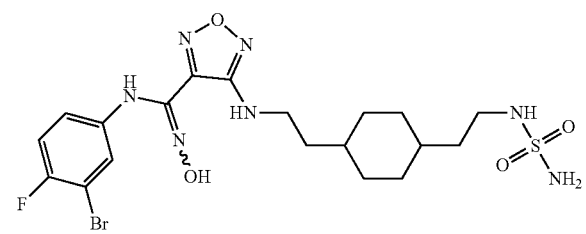
9
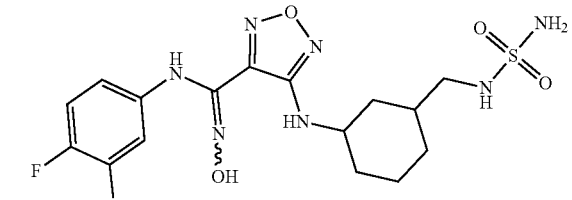
10
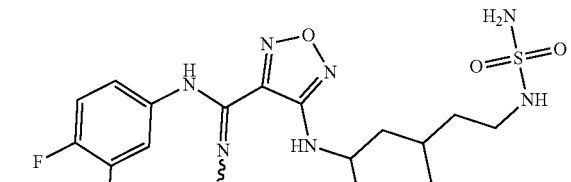
11
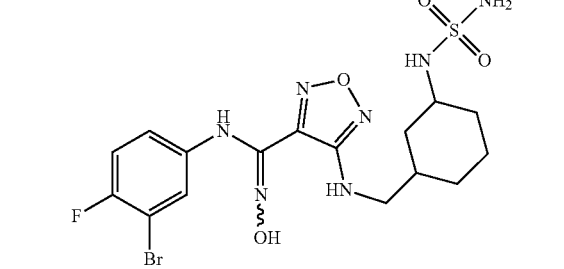
12
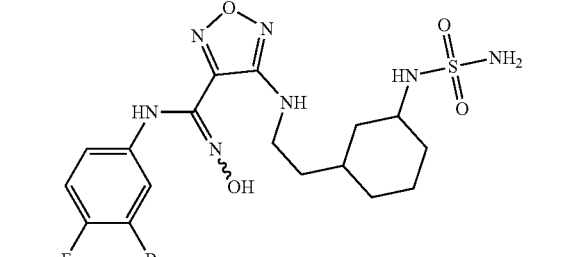
13
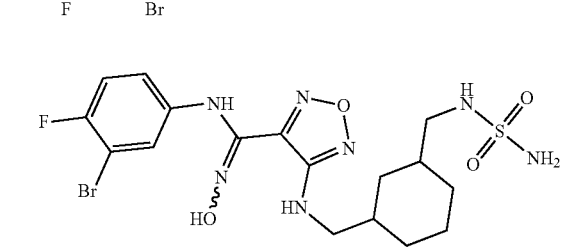

14
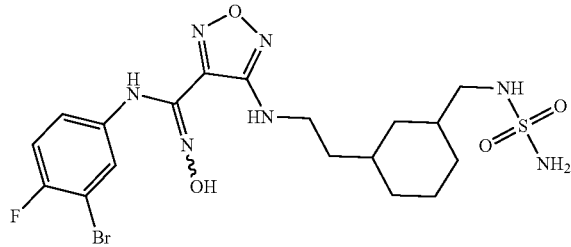
15
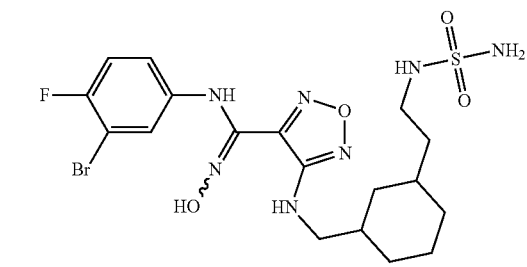
16
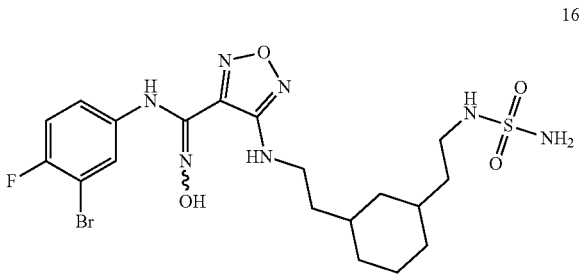
17
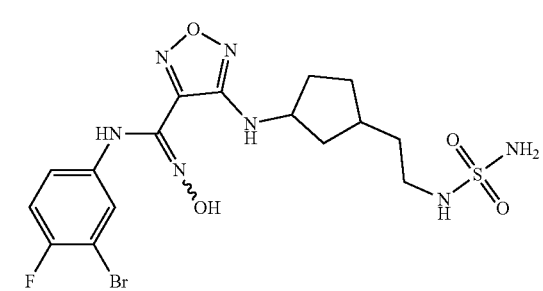
18
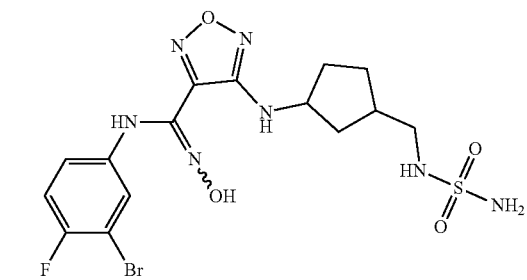
19
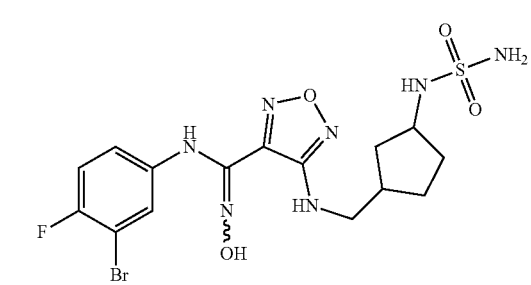
20
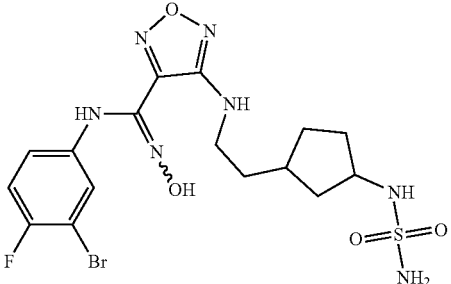
21
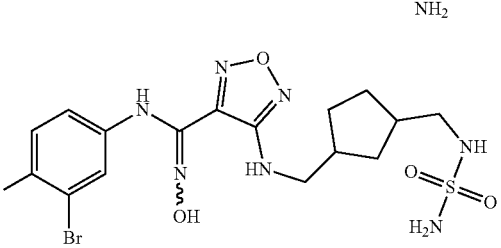
22
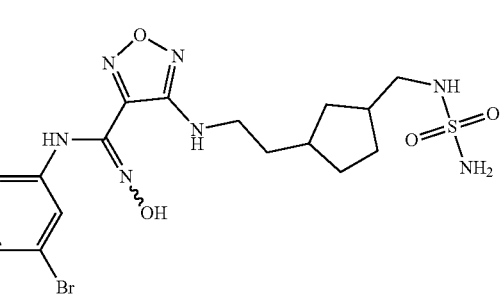
23
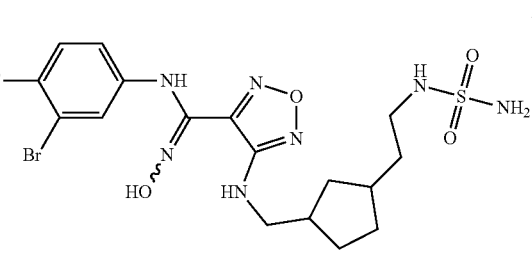
24
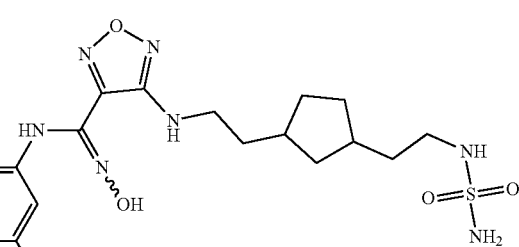
25
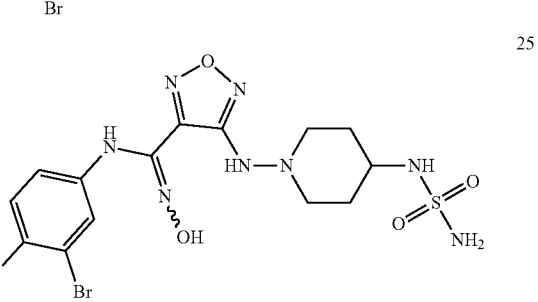

-continued
26
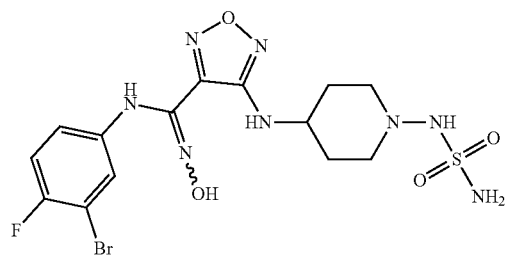
27
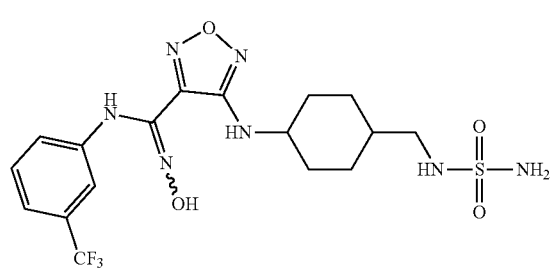
28
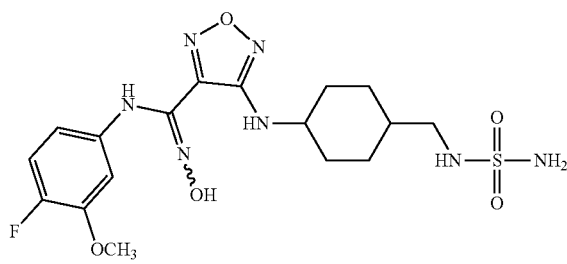
29
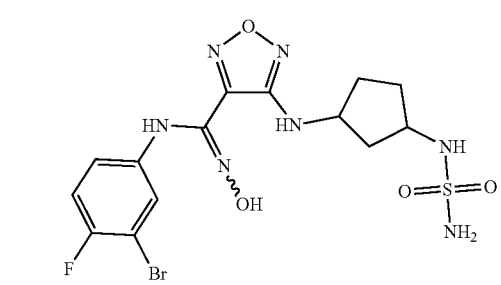
30
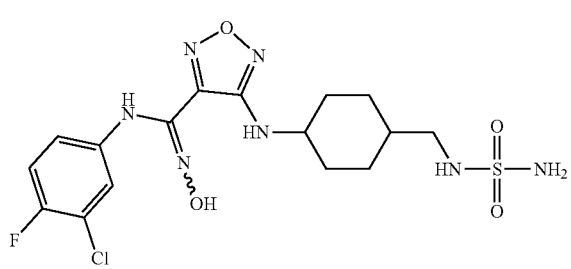
-continued
31
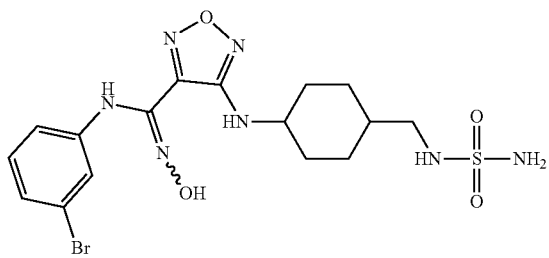
32
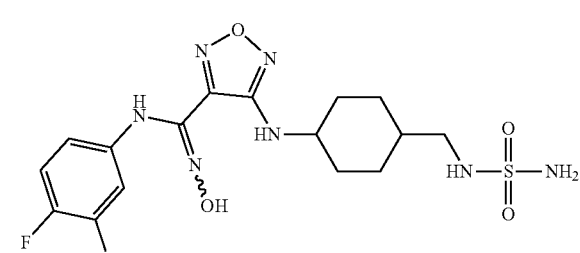
33
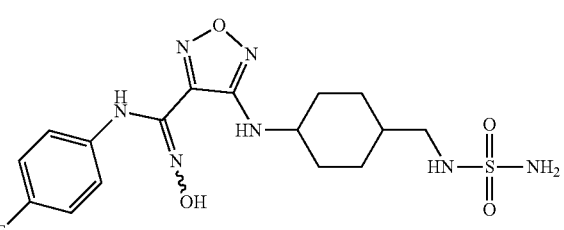
34
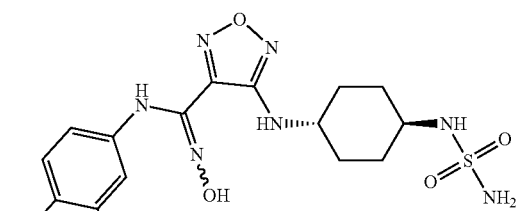
35
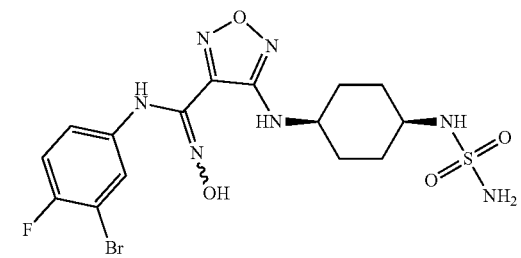
36

6. A method for manufacturing a compound of formula I according to claim 1, wherein the compound is prepared through the following route:

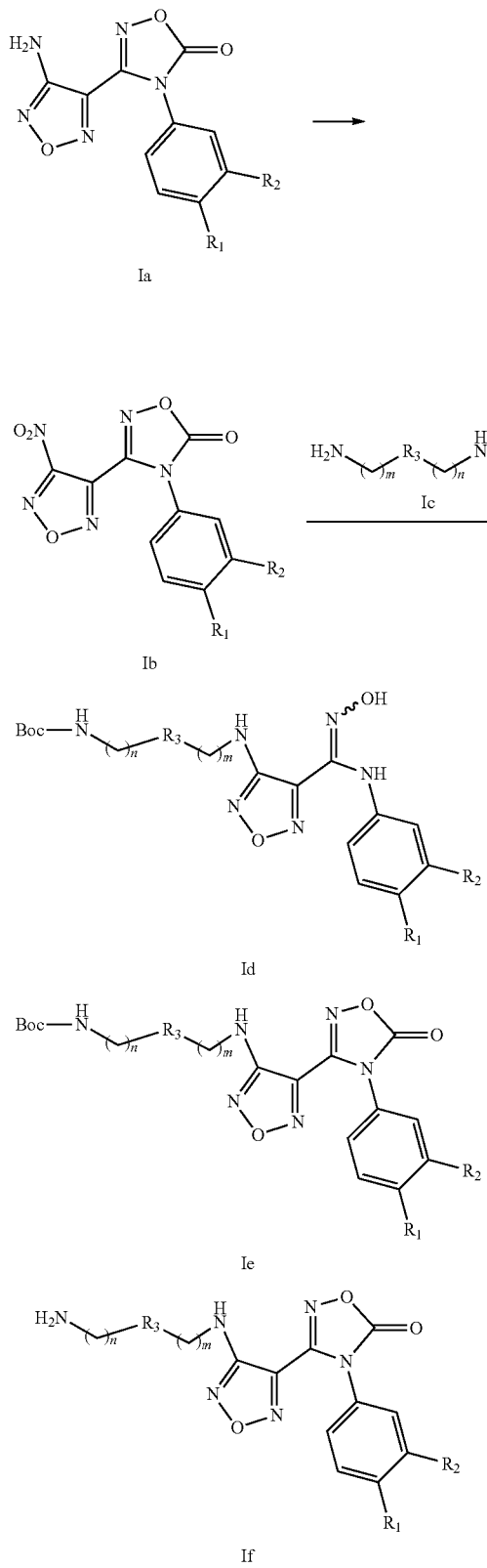

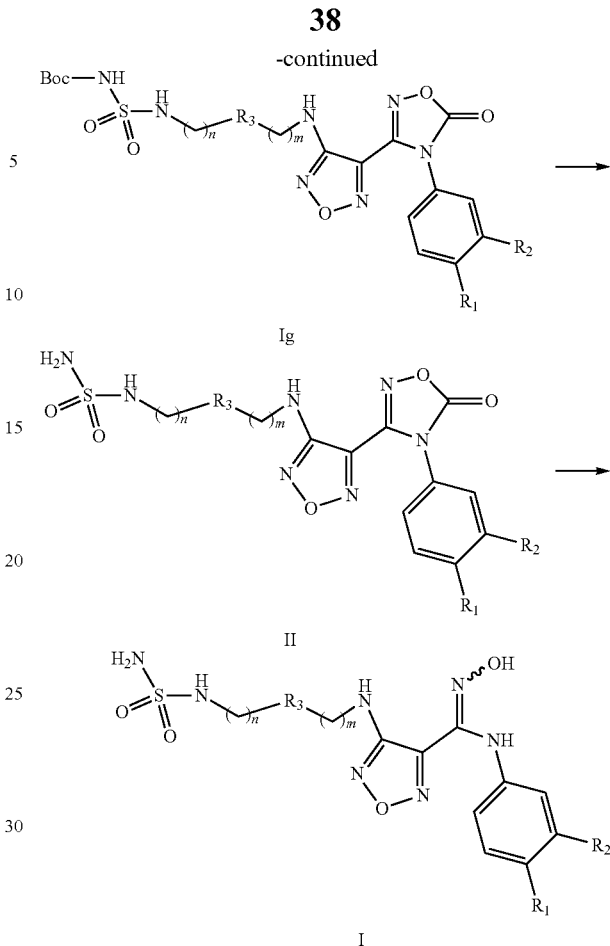

wherein, a bond represented by a wavy line "⁓" indicates the structure which represents independently a cis-isomer or a trans-isomer or a mixture of the cis and trans isomers; $R_1$ and $R_2$ are each independently selected from the group consisting of H, halogen, alkyl, alkoxyl, and haloalkyl; $R_3$ is selected from the group consisting of cyclopentyl, cyclohexyl, piperazinyl, and piperidyl; and the substitution positions of $R_3$ are optionally substituted at 1,2 position, 1,3 position or 1,4 position; m and n are each an integer number independently selected from 0 to 5.

7. The compound for inhibiting IDO according to claim 1, wherein the compound is incorporated in a preparation of a pharmaceutical composition for preventing and/or treating an IDO-mediated disease with pathologic features of a tryptophan metabolic pathway.

8. The compound for inhibiting IDO according to claim 7, wherein the pharmaceutical composition consists of an amount of the compound with therapeutic potency, wherein the compound is selected from the group consisting of tautomer, raceme, enantiomer, diastereomer, or a mixture thereof, or pharmaceutically acceptable salts thereof, or one or more pharmaceutically-acceptable carrier, diluent or excipient.

9. The compound for inhibiting IDO according to claim 7, wherein the IDO-mediated disease is selected from the group consisting of cancer, myelodysplastic syndrome, Alzheimer's disease, autoimmune diseases, depressive disorder, anxiety disorders, cataracts, psychological disorders, and AIDS.

10. The compound for inhibiting IDO according to claim 9, wherein the cancer comprises hepatocellular carcinoma, bile duct carcinoma, nasopharyngeal carcinoma, breast cancer, cervical cancer, non-small cell lung cancer, small cell lung cancer, gastric cancer, esophageal cancer, colorectal cancer, pancreatic cancer, melanoma, oral cancer, renal cancer, bladder cancer, prostate cancer, osteosarcoma, ovarian, fallopian tube cancer, gastrointestinal stromal tumor, glioma, head and neck cancer, leukemia, lymphoma, multiple myeloma and myelodysplastic syndrome.

* * * * *